United States Patent [19]

Van Scott et al.

[11] 4,367,224

[45] Jan. 4, 1983

[54] STABLE DITHRANOL COMPOSITIONS IN ANHYDROUS VEHICLES

[76] Inventors: Eugene J. Van Scott, 1138 Sewell La., Rydal, Pa. 19046; Ruey J. Yu, 4 Lindenwold Ave., Ambler, Pa. 19002

[21] Appl. No.: 263,285

[22] Filed: May 13, 1981

[51] Int. Cl.$^3$ ............... A61K 31/00; A61K 31/05; A61K 47/00
[52] U.S. Cl. ............... 424/175; 424/240; 424/346; 424/365
[58] Field of Search ............ 424/175, 346, 365, 240

[56] References Cited
U.S. PATENT DOCUMENTS 4,287,214  9/1981  Van Scott et al. ............ 424/346

OTHER PUBLICATIONS

Chemical Abstracts 78:75809q (1973).
Chemical Abstracts 67:2878z (1967).
Sagarin-Cosmetics, Science & Technology, 1957, pp. 1066–1067.

Primary Examiner—Leonard Schenkman
Attorney, Agent, or Firm—LeBlanc, Nolan, Shur & Nies

[57] ABSTRACT

Stable dithranol compositions in anhydrous vehicles therapeutically effective as topical treatment for skin disorders such as psoriasis, eczema and seborrheic dermatitides are disclosed. Incorporation of oxalic acid in anhydrous dithranol compositions has been found to chemically stabilize said dithranol. Oxalic acid may be present in an amount of from 0.01-to-2 percent by weight of the total composition. The anhydrous vehicle includes an anhydrous base formulated from glyceryl monostearate and isopropyl myristate or isopropyl palmitate as major ingredients.

20 Claims, No Drawings

STABLE DITHRANOL COMPOSITIONS IN ANHYDROUS VEHICLES

Dithranol, also known as anthralin, has been shown to be topically effective in the treatment of psoriasis, eczemas, dermatophytoses, alopecia areata and other skin disorder.

The existing dithranol products may be classified into two types: (a) water containing cream (b) petrolatum base. The water containing dithranol compositions are readily spreadable, and easy to use. However, the dithranol is not chemically stable in such compositions. Reducing agents such as BHT (butylated hydroxytoluene), BHA (butylated hydroxyanisole), and ascorbic acid, sodium bisulfite, sodium metabisulfite, stannous chloride and salicylic acid may be added to the dithranol compositions. The above reducing agents, however, cannot prevent air oxidation of dithranol in water containing compositions.

The dithranol product in petrolatum base is more stable in air oxidation but it spreads with difficulty when topically applied to the skin. The dithranol in petrolatum base also feels greasy on touching to the skin.

In our prior patent application entitled, Dithranol Compositions Stabilized with Alpha Hydroxyacids, Ser. No. 78,181, filed Sept. 24, 1979 now U.S. Pat. No. 4,287,214, we described that certain alpha hydroxyacids such as tartronic acid, mucic acid, tartaric acid and saccharic acid can chemically stabilize dithranol compositions. Although these alpha hydroxyacids can stabilize dithranol compositions containing water such as water-in-oil emulsions the best results were achieved when the dithranol compositions were formulated in anhydrous vehicles. Since the petrolatum base was too sticky to use, the anhydrous vehicles used in the compositions consisted of glyceryl monostearate and isopropyl myristate or isopropyl palmitate as major ingredients.

We have now discovered that one of the dicarboxylic acids, oxalic acid, can also chemically stabilize dithranol compositions in anhydrous vehicles. The stable dithranol compositions thus formulated have been found to be therapeutically effective for the topical treatment of skin disorders such as psoriasis, eczema and seborrheic dermatitides.

In addition to oxalic acid as a primary stabilizer for dithranol compositions other agents such as certain alpha hydroxyacids, salicylic acid, ascorbic acid, BHT, BHA, sodium bisulfite, sodium metabisulfite and stannous chloride may be added to an anhydrous composition as a secondary stabilizer.

Oxalic acid is a well known antioxidant used as a preservative in cosmetics. See *Cosmetics: Science and Technology*, Sagarin, Interscience Publishers, Inc., New York (1957). In the above publication antioxidants are classified as Phenolic type, Quinone type; Amine type; organic acids, alcohols, and esters; and inorganic acids and their salts. Oxalic acid is grouped as an organic acid with compounds such as ascorbic acid, citric acid, malic acid, tartaric acid and several others. Preferred antioxidants for use with fats and oils are said to be those in the first two classes with the remaining three classes being not too effective alone. However, members of the remaining three classes, including oxalic acid, were recognized as having a synergistic effect in combination with representatives of the first two groups.

Although the mechanism whereby oxalic acid, alone, or in combination with secondary stabilizers, functions to stabilize dithranol is not known with certainty, the antioxidant characteristics are clearly not determinative. In separate tests many antioxidants identified in the above reference, including many in the same grouping with oxalic acid were found to be totally ineffective as stabilizing agents for dithranol.

Accordingly, it is an object of this invention to provide anhydrous dithranol compositions stabilized with oxalic acid for topical application to alleviate the symptoms of skin disorders in humans.

It is another object of this invention to provide a method for effectively stabilizing dithranol compositions for topical treatment of cutaneous diseases.

These and other objects will become readily apparent with reference to the following description.

PREPARATION OF THE THERAPEUTIC COMPOSITIONS

Stable anhydrous dithranol ointments may be formulated from petrolatum, mineral oil, oxalic acid and dithranol. Petrolatum and mineral oil are heated to 70° C. until the mixture is completely melted. Oxalic acid and dithranol are added to the melt with agitation. Continue agitation during the cooling process until the mixture is congealed to a yellowish ointment.

A preferred dithranol ointment may be formulated from petrolatum 65 g, mineral oil 34.5 g, oxalic acid 0.4 g and dithranol 0.1 g. Although 0.1% dithranol ointment thus formulated is stable to air oxidation, the product feels sticky on the skin after topical application. Nonsticky and stable anhydrous dithranol creams may be formulated as follows.

Glyceryl monostearate, nonbleached flake form and isopropyl myristate or isopropyl palmitate are heated to about 70° C. until the mixture is completely melted. Oxalic acid and dithranol are added to the melt with agitation. Continue agitation during the cooling process until the mixture is congealed to a yellowish cream.

The concentration of glyceryl monostearate may range from 10-to-30% by weight of the total composition. The preferred concentration is, however, from 15-to-25%.

The concentration of isopropyl myristate or isopropyl palmitate may range from 40-to-90% by weight of the total composition. The preferred concentration is, however, from 50-to-80%.

The concentration of oxalic acid may range from 0.01-to-2% by weight of the total composition. The preferred concentration is, however, from 0.02-to-1%.

The concentration of dithranol may range from 0.01-to-1% by weight of the total composition. The preferred concentration is, however, from 0.05-to-0.5%.

In order to increase the occlusiveness of the composition, petrolatum and mineral oil may be incorporated into the formulation. In this instance glyceryl monostearate, petrolatum, mineral oil and isopropyl myristate or isopropyl palmitate are heated to about 70° C. until the mixture is completely melted. Oxalic acid and dithranol are added to the melt as described above. The concentrations of petrolatum and mineral oil may range from 0-to-30% by weight of the total composition. The preferred concentration is, however, from 5-to-15%.

Stable dithranol compositions of the instant invention may also be formulated in a solution form. In this case, dithranol and oxalic acid are dissolved in a solution formulated from a group selected from acetone, ethanol, isopropyl myristate, isopropyl palmitate, diisopropyl adipate, squalane and silicone fluid.

In our U.S. Patent application entitled, Therapeutic Compositions and Vehicles for Topical Pharmaceuticals, Ser. No. 77,726 filed Sept. 21, 1979 now U.S. Pat. No. 4,316,902, a stable anhydrous vehicle is disclosed. This invention contemplates use of that vehicle also and the disclosure thereof is hereby incorporated by reference.

In addition to oxalic acid as a primary stabilizer for dithranol compositions other agents such as certain alpha hydroxyacids, salicylic acid, ascorbic acid, BHT, BHA, sodium bisulfite, sodium metabisulfite and stannous chloride may be added to an anhydrous composition as a secondary stabilizer. The mentioned alpha hydroxyacids include tartronic acid, tartaric acid, mucic acid, citric acid, malic acid and quinic acid.

The concentration of the secondary stabilizer may range from 0.01-to-1% by weight of the total composition. The preferred concentration is, however, from 0.05-to-0.5%.

Other dermatologic drugs or agents may also be incorporated into the dithranol composition of the instant invention. The dermatologic drugs or agents include corticosteroids such as hydrocortisone, hydrocortisone 17-valerate and hydrocortisone 17-butyrate, and urea.

The following are illustrative examples for formulating anhydrous dithranol compositions stabilized with oxalic acid of this invention. It should be understood that the examples are illustrative only and not limitative of the invention.

EXAMPLE 1

Dithranol 0.1% ointment may be formulated as follows.

Petrolatum 65 g and mineral oil 34.5 g are heated to 70° C. until the mixture is completely melted. Oxalic acid 0.4 g and dithranol 0.1 g are added to the melt with agitation. Continue agitation during the cooling process until the mixture is congealed to a yellowish ointment.

EXAMPLE 2

Dithranol 0.05% cream may be formulated as follows.

Glyceryl monostearate, unbleached flake form 20 g and isopropyl myristate or isopropyl palmitate 79.75 g are heated to 70° C. until the mixture is completely melted. Oxalic acid 0.2 g and dithranol 0.05 g are added to the melt with agitation. Continue agitation during the cooling process until the mixture is congealed to a yellowish cream. The stable anhydrous cream thus formulated contains 0.05 % dithranol as an active ingredient.

EXAMPLE 3

Dithranol 0.07% cream may be formulated as follows.

Glyceryl monostearate 20 g, petrolatum 10 g, mineral oil 10 g and isopropyl myristate or isopropyl palmitate 59.73 g ae heated to 70° C. until the mixture is completely melted. Oxalic acid 0.2 g and dithranol 0.07 g are added to the melt with agitation. Continue agitation during the cooling process until the mixture is congealed to a yellowish cream.

EXAMPLE 4

Dithranol 0.1% cream may be formulated as follows.
Glyceryl monostearate 20 g, petrolatum 15 g, mineral oil 5 g and isopropyl palmitate or isopropyl myristate 59.5 g are heated to 70° C. until the mixture is completely melted. Oxalic acid 0.4 g and dithranol 0.1 g are added to the melt with agitation. Continue agitation during the cooling process until the mixture is congealed to a yellowish cream.

EXAMPLE 5

Dithranol 0.07% cream stabilized with both primary and secondary stabilizers may be formulated as follows.

Glyceryl monostearate 20 g petrolatum 10 g, mineral oil 10 g and isopropyl myristate or isopropyl palmitate 59.53 g are heated to 70° C. until the mixture is completely melted. Oxalic acid 0.2 g, mucic acid 0.2 g and dithranol 0.07 g are added to the melt with agitation. Continue agitation during the cooling process until the mixture is congealed to a yellowish cream.

EXAMPLE 6

Dithranol 0.07% composition stabilized with oxalic acid and two alpha hydroxyacids may be formulated as follows.

Glyceryl monostearate 20 g, petrolatum 10 g, mineral oil 10 g and isopropyl palmitate or isopropyl myristate 59.03 g are heated to 70° C. until the mixture is completely melted. Oxalic acid 0.2 g, tartronic acid 0.2 g, mucic acid 0.5 g and dithranol 0.07 g are added to the melt with agitation. Continue agitation during the cooling process until the mixture is congealed to a yellowish cream.

EXAMPLE 7

Dithranol 0.1% composition stabilized with oxalic acid and three alpha hydroxyacids may be formulated as follows.

Glyceryl monostearate 20 g, petrolatum 10 g, mineral oil 10 g and isopropyl myristate or isopropyl palmitate 59.1 g are heated to 70° C. until the mixture is completely melted. Oxalic acid 0.2 g, tartronic acid 0.2 g, tartaric acid 0.2 g, mucic acid 0.2 g and dithranol 0.1 g are added to the melt with agitation. Continue agitation during the cooling process until the mixture is congealed to a yellowish cream.

EXAMPLE 8

Dithranol 0.05% composition stabilized with oxalic acid and salicylic acid may be formulated as follows.

Glyceryl monostearate 20 g, petrolatum 10 g, mineral oil 10 g and isopropyl myristate or isopropyl palmitate 59.25 g are heated to 70° C. until the mixture is completely melted. Oxalic acid 0.2 g, salicylic acid 0.5 g and dithranol 0.05 g are added to the melt with agitation. Continue agitation during the cooling process until the mixture is congealed to a yellowish cream.

EXAMPLE 9

Dithranol 0.07% composition stabilized with oxalic acid and ascorbic acid may be formulated as follows.

Glyceryl monostearate 20 g, petrolatum 10 g, mineral oil 10 g and isopropyl myristate or isopropyl palmitate 59.23 g are heated to 70° C. until the mixture is completely melted. Oxalic acid 0.2 g, ascorbic acid 0.5 g and dithranol 0.07 g are added to melt with agitation. Continue agitation during the cooling process until the mixture is congealed to a yellowish cream.

EXAMPLE 10

Dithranol 0.1% composition stabilized with oxalic acid, salicylic acid and ascorbic acid may be formulated as follows.

Glyceryl monostearate 20 g, petrolatum 10 g, mineral oil 10 g and isopropyl myristate or isopropyl palmitate 58.7 g are heated to 70° C. until the mixture is completely melted. Oxalic acid 0.2 g, salicylic acid 0.5 g, ascorbic acid 0.5 g and dithranol 0.1 g are added to the melt with agitation. Continue agitation during the cooling process until the mixture is congealed to a yellowish cream.

EXAMPLE 11

Dithranol 0.07% composition stabilized with oxalic acid, two alpha hydroxyacids and salicylic acid may be formulated as follows.

Glyceryl monostearate 20 g, petrolatum 10 g, mineral oil 10 g and isopropyl myristate or isopropyl palmitate 58.83 g are heated to 70° C. until the mixture is completely melted. Oxalic acid 0.2 g tartronic acid 0.2 g, mucic acid 0.2 g, salicylic acid 0.5 g and dithranol 0.07 g are added to the melt with agitation. Continue agitation during the cooling process until the mixture is congealed to a yellowish cream.

EXAMPLE 12

Dithranol 0.07% composition stabilized with oxalic acid, three alpha hydroxyacids, salicylic acid and ascorbic acid may be formulated as follows.

Glyceryl monostearate 20 g, petrolatum 10 g, mineral oil 10 g and isopropyl myristate or isopropyl palmitate 58.13 g are heated to 70° C. until the mixture is completely melted. Oxalic acid 0.2 g, tartronic acid 0.2 g, tartaric acid 0.2 g, mucic acid 0.2 g, salicylic acid 0.5 g, ascorbic acid 0.5 g and dithranol 0.07 g are added to the melt with agitation. Continue agitation during the cooling process until the mixture is congealed to a yellowish cream.

EXAMPLE 13

Dithranol 0.05% solution stabilized with oxalic acid may be formulated as follows.

Dithranol 0.05 g and oxalic acid 0.1 g are dissolved in acetone 20 ml and isopropyl myristate or isopropyl palmitate 79.85 ml. The yellowish solution thus prepared may be stored in amber dropper bottles.

EXAMPLE 14

Dithranol 0.1% solution stabilized with oxalic acid and salicylic acid may be formulated as follows.

Dithranol 0.1 g, oxalic acid 0.2 g and salicylic acid 0.5 g are dissolved in acetone 20 ml and isopropyl myristate or isopropyl palmitate 79.2 ml. The yellowish solution thus prepared may be stored in amber dropper bottles.

EXAMPLE 15

Dithranol 0.07% composition containing 1% hydrocortisone may be formulated as follows.

Glyceryl monostearate 20 g, petrolatum 10 g, mineral oil 10 g and isopropyl myristate or isopropyl palmitate 58.03 g are heated to 70° C. until the mixture is completely melted. Oxalic acid 0.4 g, mucic acid 0.5 g, dithranol 0.07 g and hydrocortisone 1 g are added to the melt with agitation. Continue agitation until the mixture is congealed to a yellowish cream.

EXAMPLE 16

Dithranol 0.08% composition containing 0.5% hydrocortisone may be formulated as follows.

Glyceryl monostearate 20 g, petrolatum 10 g, mineral oil 10 g and isopropyl myristate or isopropyl palmitate 57.82 g are heated to 70° C. until the mixture is completely melted. Oxalic acid 0.4 g, tartronic acid 0.2 g, mucic acid 0.5 g, salicylic acid 0.5 g, hydrocortisone 0.5 g and dithranol 0.08 g are added to the melt with agitation. Continue agitation until the mixture is congealed to a yellowish cream.

EXAMPLE 17

Dithranol 0.05% composition containing 0.2% hydrocortisone 17-valerate may be formulated as follows.

Glyceryl monostearate 20 g, petrolatum 10 g, mineral oil 10 g and isopropyl myristate or isopropyl palmitate 58.85 g are heated to 70° C. until the mixture is completely melted. Oxalic acid 0.2 g, tartronic acid 0.2 g, salicylic acid 0.5 g, dithranol 0.05 g and hydrocortisone 17-valerate 0.2 g are added to the melt with agitation. Continue agitation until the mixture is congealed to a yellowish cream.

TEST RESULTS

(A) Chemical Stability

Generally, a dithranol composition shows a bright yellowish color when it is freshly prepared in a solution, a cream, an ointment or a paste. Without addition of any stabilizers the composition which contains dithranol will change in color from yellowish to brown at room temperature in a matter of a few days to a few weeks depending on whether the composition contains water or not. For example, dithranol 0.05% in hydrophilic ointment USP changed in color from yellow to gray within 24 hours at room temperature, and the composition turned to brown color within 48 hours. Under the same conditions, dithranol 0.05% in petrolatum base changed in color slowly from bright yellow to grayish yellow within 24 hours at room temperature, and the ointment turned into a brown color after 12 days.

It has been shown that a dithranol composition is therapeutically efficacious as long as the composition does not change in color from yellowish to brownish. Therefore, the simplest method to ascertain whether a substance is a dithranol stabilizer or not is to determine whether the yellowish color of the composition is maintained.

In order to determine the dithranol stabilizing effect of the present invention, oxalic acid at various concentrations was incorporated into the compositions containing dithranol prepared according to Examples. Each test cream or ointment was stored in a two ounce glass jar and a one ounce transparent glass jar. The two ounce glass jar was left at room temperature and the one ounce transparent glass jar was kept at 45° C. for an extended period of time.

A test substance is determined to be a dithranol stabilizer when an anhydrous dithranol composition which also contains the test substance does not change yellowish color at 45° C. for more than one month.

A test substance is determined to be a nonstabilizer if the anhydrous test composition containing both the dithranol and the test substance changes in color from yellowish to dark brownish within one month at 45° C.

Based on the above criteria we have found that oxalic acid was a satisfactory stabilizer for dithranol formulations in anhydrous compositions, i.e., the composition remained bright yellowish in color at 45° C. for more than one month.

Under the same test conditions we have also found that the following common antioxidants were not satisfactory stabilizers for dithranol formulations. These antioxidants are butylated hydroxyanisole (BHA), butylated hydroxytoluene (BHT), gallic acid, propyl gallate, tocopherol, tocopherol acetate, casein, ethanolamine, glutamic acid, lecithin, mannitol and sorbitol.

(B) Clinical Test

The involved skin in psoriasis is hyperplastic (thickened). erythematous (red or inflammed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied therapeutic test materials as follows:

|  | DEGREE OF IMPROVEMENT | | | | |
| --- | --- | --- | --- | --- | --- |
|  | None (0) | Mild (1+) | Moderate (2+) | Substantial (3+) | Complete (4+) |
| Thickness | Highly Elevated | Detectable reduction | Readily apparent | Barely elevated | Normal thickness |
| Texture | Visibly rough | Palpably rough | Uneven but not rough | Slightly uneven | Visibly and palpably smooth |
| Color | Intense red | Red | Dark pink | Light pink | Normal skin color |

In order to ascertain whether the dithranol compositions stabilized with oxalic acid are therapeutically efficacious for topical treatment of psoriasis, a total of more than 20 patients having psoriasis were treated in this study.

Therapeutic compositions of dithranol stabilized with oxalic acid and with or without incorporation of corticosteroids were prepared according to the Examples. Treatment areas in patients having psoriasis were localized lesions 4–15 cm in diameter. The medicinal creams were topically applied by the patient in an amount sufficient to cover the treatment site. Applications were made two-three times daily and without occlusive dressing. Clinical evaluations of degrees of improvement were made at weekly or biweekly intervals. Treatment periods generally lasted for six weeks, unless clearing of disease occured earlier and an evaluation of degree of improvement was made at that time. The treatment results on psoriatic patients are summarized in the following table.

| Effects[a] on Psoriasis of Topical Dithranol Compositions Stabilized with Oxalic Acid | | | |
| --- | --- | --- | --- |
| Dithranol Concentration % | Corticosteroid Concentration % | Number of Patients | Average Therapeutic Efficacy |
| 0.05 | 0 | 12 | 2+ |
|  | 1[b] | 9 | 3+ |
| 0.07 | 0 | 8 | 3+ |
|  | 1[b] | 7 | 4+ |
|  | 0.2[c] | 10 | 4+ |
| 0.1 | 0 | 15 | 3+ |
|  | 0.5[b] | 12 | 4+ |

[a]The clinical evaluations were made at the end of six week topical application.
[b]Hydrocortisone
[c]Hydrocortisone 17-valerate.

As shown by the above table, all dithranol compositions, stabilized with oxalic acid, caused moderate or substantial improvements in the patients tested. With the incorporation of hydrocortisone or hydrocortisone 17-valerate all dithranol compositions gave substantial or complete improvement in the patients treated.

Psoriatic patients with scalp involvement and patients having seborrheic dermatitis on the scalp were instructed to apply topically a dithranol solution stabilized with oxalic acid on the involved area of the scalp. Applications were made two times daily and without any kind of additional treatment. Test periods usually lasted for six weeks, and applications were discontinued at any time when resolution of the lesions on the scalp were clinically judged to be complete.

In most cases, the affected scalp of psoriatic patients and patients having seborrheic dermatitis became less flaky and less erythematous after a few weeks of topical treatment.

In order to determine whether the dithranol compositions stabilized with oxalic acid are therapeutically efficacious for topical treatment of eczema, three patients having eczema were treated in another study. Conditions and schedules for treatment of eczema were the same as that of psoriasis. In all three patients tested, dithranol compositions stabilized with oxalic acid caused substantial improvement after six weeks of topical treatment.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. In an anhydrous composition containing an antiinflammatory effective amount of dithranol in a pharmaceutically acceptable vehicle for topical application, the improvement comprising a stabilizing effective amount of oxalic acid present as a primary stabilizer for dithranol in said composition.

2. The composition of claim 1, further comprising at least one secondary stabilizer, present in a stabilizing effective amount in said composition, selected from the group consisting of tartaric acid, tartronic acid, mucic acid, malic acid, citric acid, quinic acid, salicylic acid, ascorbic acid, sodium bisulfite, sodium metabisulfite, stannous chloride, butylated hydroxyanisole, and butylated hydroxytoluene.

3. The composition of claim 1, further comprising an antiinflammatory effective amount of at least one member selected from the group consisting of hydrocortisone, hydrocortisone 17-valerate, and hydrocortisone 17-butyrate.

4. The composition of claim 1, wherein oxalic acid is present in a concentration of from about 0.01 to about 2 percent by weight of the total concentration.

5. The composition of claim 2, wherein the secondary stabilizer is present in from about 0.01 to about 1 percent by weight of the total composition.

6. The composition of claim 1, wherein dithranol is present in a concentration of about 0.01 to about 1 percent by weight of the total composition.

7. The composition of claim 1, wherein the vehicle is a liquid solution containing at least one member selected from the group consisting of acetone, ethanol, isopropyl myristate, isopropyl palmitate, diisopropyl adipate, squalane and silicone fluid.

8. The composition of claim 1, wherein the vehicle comprises a mixture of glyceryl monostearate, and isopropyl myristate or isopropyl palmitate present in a concentration range of about 10 to 30%, and 40 to 90% by weight, respectively.

9. The composition of claim 8, further comprising up to 30% by weight of at least one member selected from the group consisting of petrolatum and mineral oil.

10. The composition of claim 1, wherein the vehicle comprises a mixture of petrolatum and mineral oil.

11. The method for stabilizing an anhydrous dithranol containing composition containing antiinflammatory effective amount of dithranol and a pharmaceutically acceptable vehicle for topical application to involved areas of the human body comprising:
  admixing in said composition a chemically stabilizing effective amount of oxalic acid as the primary stabilizer.

12. The method of claim 11, further comprising admixing at least one secondary stabilizer, present in a stabilizing effective amount in said composition, selected from the group consisting of tartaric acid, tartronic acid, mucic acid, malic acid, citric acid, quinic acid, salicylic acid, ascorbic acid, sodium bisulfite, sodium metabisulfite, stannous chloride, butylated hydroxyanisole, and butylated hydroxytoluene.

13. The method of claim 11, further comprising admixing an antiinflammatory effective amount of at least one member selected from the group consisting of hydrocortisone, hydrocortisone 17-valerate, and hydrocortisone 17-butyrate in said composition.

14. The method of claim 11, wherein oxalic acid is present in a concentration of from about 0.01 to about 2 percent by weight of the total concentration.

15. The method of claim 12, wherein the secondary stabilizer is present in from about 0.01 to about 1 percent by weight of the total composition.

16. The method of claim 11, wherein dithranol is present in a concentration of about 0.01 to about 1 percent by weight of the total composition.

17. The method of claim 11, wherein the vehicle is a liquid solution containing at least one member selected from the group consisting of acetone, ethanol, isopropyl myristate, isopropyl palmitate, diisopropyl adipate, squalane and silicon fluid.

18. The method of claim 11, wherein the vehicle comprises a mixture of glyceryl monostearate, and isopropyl myristate or isopropyl palmitate present in a concentration range of about 10 to 30% and 40 to 90% by weight, respectively.

19. The method of claim 18, further comprising up to 30% by weight of at least one member selected from the group consisting of petrolatum and mineral oil.

20. The method of claim 11, wherein the vehicle comprises a mixture of petrolatum and mineral oil.

* * * * *